United States Patent
Chen et al.

(10) Patent No.: US 7,265,243 B2
(45) Date of Patent: Sep. 4, 2007

(54) CATALYTIC OXACYLATION VAPOR PHASE PROCESS

(75) Inventors: Shien-Chang Chen, Taipei (TW); Fu-Shen Lin, Kaohsiung (TW); Liang-An Hsu, Kaohsiung (TW); Pi-Fwu Jang, Kaohsiung (TW)

(73) Assignee: Dairen Chemical Corporation, Taipei (TW)

( * ) Notice: Subject to any disclaimer, the term of this patent is extended or adjusted under 35 U.S.C. 154(b) by 97 days.

(21) Appl. No.: 10/791,646

(22) Filed: Mar. 1, 2004

(65) Prior Publication Data

US 2004/0236121 A1    Nov. 25, 2004

Related U.S. Application Data

(62) Division of application No. 09/454,316, filed on Dec. 3, 1999, now abandoned.

(30) Foreign Application Priority Data

Aug. 30, 1999    (TW) ................................ 88114793 A

(51) Int. Cl.
    *C07C 67/05*    (2006.01)
(52) U.S. Cl. ..................................... 560/245
(58) Field of Classification Search ............... 502/151, 502/170, 344, 207, 339; 560/243, 245
    See application file for complete search history.

(56) References Cited

U.S. PATENT DOCUMENTS

| | | | |
|---|---|---|---|
| 3,655,747 A | 4/1972 | Sennewald et al. | |
| 3,822,308 A | 7/1974 | Kronig et al. | |
| 3,917,676 A | 11/1975 | Kisaki et al. | |
| 3,925,452 A | 12/1975 | Swodenk et al. | |
| 4,158,737 A * | 6/1979 | Bartsch | 560/245 |
| 4,571,431 A | 2/1986 | Drake | |
| 4,647,690 A | 3/1987 | Drake | |
| 5,011,980 A | 4/1991 | Sano et al. | |
| 5,731,457 A * | 3/1998 | Nicolau et al. | 560/245 |
| 5,808,136 A * | 9/1998 | Tacke et al. | 560/243 |

FOREIGN PATENT DOCUMENTS

EP    0 361 484 A2    4/1990

* cited by examiner

*Primary Examiner*—Edward M. Johnson
(74) *Attorney, Agent, or Firm*—Edwards Angell Palmer & Dodge LLP; Peter F. Corless; Dwight D. Kim

(57) ABSTRACT

This invention relates to a catalyst which comprises palladium metal as the main catalyst, tin metal or a mixture of tin and additional metals as the promoter, in combination with an alkali or alkaline earth metal compound, supported on the outer surface of a porous carrier. The catalyst is used in the process for producing allyl acetate through the oxacylation of propylene, acetic acid and oxygen in a vapor phase. The catalyst of the present invention exhibits high catalytic activity, high catalytic selectivity and high catalytic life, which greatly increases the economic utility of the oxacylation process.

9 Claims, No Drawings

CATALYTIC OXACYLATION VAPOR PHASE PROCESS

The present application is a Divisional application of U.S. Ser. No. 09/454,316, filed Dec. 3, 1999, now abandoned which in turn claimed the prior benefit of Taiwan Application 88114793, filed Aug. 30, 1999, each of which is incorporated herein by reference in its entirety.

FIELD OF THE INVENTION

This invention relates to a catalyst which is comprised of palladium metal as the main catalyst, tin metal or a mixture of tin and additional metal(s) as the promoter, in combination with an alkali or alkaline earth metal compound, supported on the outer surface of a porous carrier. The catalyst is used in the process for producing allyl acetate through the oxacylation of propylene, acetic acid and oxygen in a vapor phase.

BACKGROUND OF THE INVENTION

Previously, in the production of allyl acetate through the oxacylation of propylene, acetic acid and oxygen in a vapor phase, a silica carrier impregnated with palladium only was the main catalyst, and alkali or alkaline earth metal compound was used as the activator (U.S. Pat. No. 3,925,452). In order to get better activity from this catalyst, the oxacylation should be performed at higher temperatures. Under these conditions, the formation of carbon dioxide byproduct was increased, and the space time yield (STY, the yield per hour per liter of the catalyst) of allyl acetate was unable to be promoted even by increasing the amounts of palladium or the activator. Generally, by only using palladium as the catalyst during the oxacylation process, the space time yield of allyl acetate would not exceed 60 (g/hr/l of catalyst), and the selectivity of such a catalyst to allyl acetate would only reach 87%. In other words, most of propylene reactant was burned into carbon dioxide or converted into other byproducts. Apparently, when only palladium and the activator were used as the catalyst, the catalytic ability of the catalyst was rather low, and waste resulted from the complete burning of propylene into carbon dioxide, which adversely influenced the industrial process.

In order to improve on this drawback, in the preparation process of the catalyst for oxacylation reaction, other metals were added so as to increase the activity and selectivity of the catalyst (U.S. Pat. No. 3,917,676). Therefore, most of the compositions of the catalysts were comprised of, not only palladium, the main catalyst, and alkali or alkaline earth metal, the activator, but also other metals, as the promoters. For example, along with catalysts with the combination of the main catalyst palladium and the promoters of potassium, bismuth and barium (U.S. Pat. No. 4,571,431), the combination of the main catalyst palladium and the promoters of copper, lead, ruthenium and rhenium (EP 0361484), etc. have been disclosed. Among these, a catalyst with the combination of the main catalyst palladium and the promoter copper exhibited higher activity and selectivity (U.S. Pat. No. 5,011,980).

For the purpose of high catalytic activity and high catalyst selectivity, besides the addition of other metals as the promoter in preparing the catalyst, a certain amount of water as a diluent should be added into the feeding materials of propylene, acetic acid and oxygen for performing the oxacylation reaction, in the traditional process of producing ally acetate. If moisture content was under a certain ratio, the catalytic activity and life of the catalyst could not be retained and would deteriorate rapidly. Usually, the addition of the water diluent would limit the yield of the final product. Further, the final product, allyl acetate, should be purified after the oxacylation, which would result in consuming and wasting energy of the whole process, and the economical effect could not be attained.

In the presence of the catalyst produced in this invention, while no water is added into the reactant materials for the oxacylation process, or only a small amount of water is added in accordance with the requirement of the process, not only will the catalytic activity and life of the catalyst be retained and not deteriorate, but a high catalytic activity and high selectivity will be attained. Therefore, the energy consumed and wasted resulting from the addition of water can be avoided, and the economical effect of the oxacylation process can be greatly increased.

SUMMARY OF THE INVENTION

This invention relates to a catalyst which is comprised of palladium metal as the main catalyst, tin metal or a mixture of tin and additional metal(s) as the promoter, in combination with an alkali or alkaline earth metal compound, supported on the outer surface of a porous carrier. The catalyst is used in the process for producing allyl acetate through the oxacylation of propylene, acetic acid and oxygen in a vapor phase. The catalyst of the present invention exhibits high catalytic activity, high catalytic selectivity and high catalytic life, which greatly increases the economic utility of the oxacylation process.

DETAILED DESCRIPTION OF THE INVENTION

The porous carriers which are suitable for preparing the catalyst for oxacylation of the present invention are alumina, silica gel, silica, active carbon, silicon carbide, diatomaceous earth, pumice and the like, while among these, silica and alumina are preferable.

The main catalyst metal of the catalyst for oxacylation of the present invention is palladium; the metal content thereof, based on the weight of the carrier, is 0.1 to 5.0 weight %, preferably 0.3 to 1.5 weight %. The promoter metal of the catalyst for oxacylation of the present invention is tin or a mixture of tin and additional metal(s) selected from the group consisting of gold, copper, cadmium, bismuth, cerium and a mixture thereof, while among these, a mixture of tin and gold is preferable; the metal content thereof, based on the weight of the carrier, is 0.01 to 5.0 weight %, preferably 0.02 to 1.0 weight %. The activator of the catalyst for oxacylation of the present invention is an alkali or alkaline earth metal compound, the examples thereof being the hydroxides, acetates, nitrates and bicarbonates of potassium, sodium, cesium, magnesium, barium and the like, while among these, potassium salts are preferable, and potassium acetate is even more preferable. The content thereof, based on the weight of the carrier, is 1 to 15 weight %, preferably 4 to 10 weight %.

Traditionally, the preparation method of the catalyst for oxacylation was essentially comprised of the following steps: (1) a carrier was impregnated with an aqueous solution of soluble palladium ions and metal ions of the promoter; (2) the impregnated carrier was immersed in an alkali solution, so that the soluble palladium ions and metal ions of the promoter were precipitated on the surface layer of the carrier and formed into insoluble oxidative state palladium and promoter metal; (3) the treated carrier was washed with water to remove soluble ions produced during the precipitation; (4) the oxidative state palladium and promoter metal supported on the treated carrier were then reduced to the metallic state; (5) the reduced carrier in (4) was impregnated with a solution of an alkali or alkaline earth metal compound; and (6) the impregnated carrier in (5) was dried. The term "oxidative state" used herein according to the present invention means a metal in a cationic state, for example, oxidative state palladium means $Pd^{2+}$.

The catalyst for oxacylation of the present invention is prepared mainly in accordance with the traditional method. After the oxidative state palladium and promoter metal are supported on the surface of the porous carrier, this not-reduced yet catalyst is placed in a reactor and the reducing step is performed under suitable reductive conditions using gaseous or liquid reducing agents. The examples of the reducing agents are amines, carbon monoxide, hydrogen, alkene, aldehydes and hydrazines. When gaseous reducing agents are used, it is preferable to dilute the gaseous reducing agent with inert gas (such as nitrogen gas) The amount of the reducing agent used depends on the amounts of the palladium and the promoter metal, the equivalents used thereof usually being at least 1 to 1.5 times of the equivalents required to reduce the catalyst. If necessary, more reducing agent can be used. After the reducing process, the reduced catalyst is washed with deionized water until the chloride ions are completely removed and then dried. After drying, the reduced catalyst is impregnated with an aqueous solution containing an alkali or alkaline earth metal compound. Finally, the catalyst is dried at a temperature between 80 to 150° C.

A certain amount of the above prepared catalyst for oxacylation is placed in a reacting tube with an inner diameter of 20 mm and a length of 2.0 m. Under a specific pressure at the inlet of the reacting tube, the reactant feeding gases are introduced into the tube at a reacting temperature set according to the activity of the catalyst. These reactant feedings comprise propylene, nitrogen, acetic acid, oxygen and water, wherein the content of propylene is 20 to 50 volume %; the content of nitrogen is 20 to 60 volume %; the content of acetic acid is 5 to 25 volume %; the content of oxygen is 5 to 10 volume %; and the content of water is 0 to 15 volume %, preferably 0 to 10 volume %. The catalyst for oxacylation of the present invention is characterized in that, the catalytic activity and life of the catalyst can be retained and will not deteriorate while no water is added into the reactant composition, or if only a small amount of water is added in the oxacylation process.

The operation temperature of the above oxacylation process is in the range of 100° C. to 250° C., preferably 140° C. to 200° C.; the operation pressure is in the range of 0 to 15 $kg/cm^2 \cdot g$, preferable 5 to 10 $kg/cm^2 \cdot g$.

The yield of allyl acetate is determined by analyzing the composition at the exit when the oxacylation process is carried out for a definite time.

Generally, the selection of a catalyst in the industry is based on the catalytic activity (STY). The catalytic activity can be calculated basically according to the following formula:

The activity of a catalyst:

$$STY(\text{space time yield}) = \frac{\text{weight of allyl acetates produced (g)}}{\text{volume (l) of catalyst} \times \text{sampling time (hr)}}$$

-continued

The selectivity of a catalyst:

$$\text{Allyl acetate selectivity} = \frac{\text{moles of allyl acetate produced}}{\text{moles of allyl acetate produced} + 1/3 \text{ moles of } CO_2 \text{ produced}}$$

It is confirmed from the evaluation of the catalytic activity in the oxacylation process' practical application that the catalyst for oxacylation prepared in accordance with the present invention not only provides higher activity of the whole oxacyltion reaction of propylene, acetic acid and oxygen, but also prolongs its own life. That is, compared to the conventional catalysts, the catalyst of the present invention is able to yield more allyl acetate per unit volume of catalyst in the reactor and per unit time, while no water or only a small amount of water is added in the oxacylation process, and the conditions of the oxacylation reaction (such as pressure, temperature, oxygen concentration) remain constant. Thus, the energy wasted resulting from the traditional process by using large amounts of water can be reduced. Moreover, if the productive yield remains constant, not only can the reacting temperature be decreased, but also the selectivity of the reaction can be higher, which leads to less production of carbon dioxide and less product loss during the removal of carbon dioxide. Thus, the unit raw material consumption will be lower. This is beneficial to the industrial production of allyl acetate.

The present invention will be further described with reference to the following Examples and Comparative Examples, but the scope of the present invention is by no means limited.

EXAMPLE 1

The carrier employed in this Example was a porous carrier of alumina/silica with an outer diameter of 5 mm and available from SUD-CHEMIE AG. This carrier had a surface area of 100 to 120 $m^2/g$, a pore volume of 0.7 to 0.9 ml/g and a bulk density of 600 g/l. The metal component-supporting catalyst was prepared according to the following steps:

Step 1): An aqueous $Na_2PdCl_4$ solution with weight of 2.2 kg containing 15 weight % of palladium was added into a mixture of an aqueous $SnCl_2$ solution with weight of 0.5 kg containing 15 weight % of tin and an aqueous $HAuCl_4$ solution with weight of 0.5 kg containing 30 weight % of gold. The mixture was then diluted with deionized water till total volume was 37.2 liters. One-hundred liters of alumina/silica carrier was placed in an impregnating tank with rotation rate of 24 turns per minute. The mixture was added into the tank rapidly.

Step 2): Hot air was passed through to dry the carrier. The temperature of the hot air was lower than 120° C.

Step 3): Twenty-eight weight % of NaOH solution (about 60 kg) was added to the dried catalyst. The originally soluble chloride state palladium, tin and gold were transformed into insoluble hydroxide state palladium, tin and gold.

Step 4): The impregnated catalyst carrier after drying was placed in a reducing reactor. The reducing gases were passed into the reactor, wherein the reducing gases could be diluted with other inert gases. The hydroxide state metal catalyst was reduced into a metallic state catalyst.

Step 5): The above catalyst was washed to remove chloride ions until the catalyst was free of chloride ions.

Step 6): The catalyst carrier was dried as in step 2).

Step 7): An adequate amount of potassium acetate was added into the dried catalyst carrier, so that each liter of the catalyst contained 30 g weight of potassium acetate.

Step 8): The catalyst carrier was dried as in step 2).

After the above steps, a catalyst containing 3.3 g/l of palladium, 0.75 g/l of tin, 1.5 g/l of gold and 30 g/l of potassium acetate was obtained, wherein all palladium, tin and gold were well distributed on the surface of the carrier.

Four hundred and fifty milliliters of the catalyst thus obtained was charged into a reacting tube with an inner diameter of 20 mm and a length of 2.0 m. Under a pressure of 7 kg/cm$^2$ (gauge pressure) at the inlet of the reactor, the reacting gaseous mixture was introduced into the reactor at a temperature of 140° C. The gaseous mixture was comprised of 41 volume % of propylene, 43 volume % of nitrogen gas, 10 volume % of acetic acid and 6 volume % of oxygen. When the composition at the exit was analyzed in a definite time, the activity and the selectivity of the catalyst were calculated. The results are listed in Table 1.

When the activity and the selectivity of the catalyst were evaluated, the crude product at the exit of the reactor was cooled with chilled water, and the composition was analyzed by Shimadzu Gas Chromatography. The flow rate of the gases was determined by Shinagawa Dry Gas Meter.

EXAMPLE 2

The catalyst was prepared by the same method as in Example 1 except that, in step 1), an aqueous $Na_2PdCl_4$ solution with weight of 2.2 kg containing 15 weight % of palladium, an aqueous $SnCl_2$ solution with weight of 0.5 kg containing 15 weight % of tin and an aqueous $CuCl_2$ solution with weight of 0.5 kg containing 15 weight % of copper were prepared.

This catalyst was evaluated by the same method as in Example 1, and the results are listed in Table 1.

EXAMPLE 3

The catalyst was prepared by the same method as in Example 1 except that, in step 1), an aqueous $Na_2PdCl_4$ solution with weight of 2.2 kg containing 15 weight % of palladium and an aqueous $SnCl_2$ solution with weight of 0.5 kg containing 15 weight % of tin were prepared.

This catalyst was evaluated by the same method as in Example 1, and the results are listed in Table 1.

EXAMPLE 4

The catalyst was prepared exactly by the same method as in Example 1, i.e., an aqueous $Na_2PdCl_4$ solution with weight of 2.2 kg containing 15 weight % of palladium, an aqueous $SnCl_2$ solution with weight of 0.5 kg containing 15 weight % of tin and an aqueous $HAuCl_4$ solution with weight of 0.5 kg containing 30 weight % of gold were prepared.

This catalyst was evaluated by the same method as in Example 1 except that, the gaseous mixture for performing oxacylation reaction was comprised of 41 volume % of propylene, 37 volume % of nitrogen gas, 9 volume % of acetic acid, 6 volume % of oxygen and 7 volume % of water, and the results are listed in Table 1.

COMPARATIVE EXAMPLE 1

The catalyst was prepared by the same method as in Example 1 except that, in step 1), an aqueous $Na_2PdCl_4$ solution with weight of 2.2 kg containing 15 weight % of palladium and an aqueous $HAuCl_4$ solution with weight of 0.5 kg containing 30 weight % of gold were prepared.

This catalyst was evaluated by the same method as in Example 4, and the results are listed in Table 1.

COMPARATIVE EXAMPLE 2

The catalyst was prepared by the same method as in Example 1 except that, in step 1), an aqueous $Na_2PdCl_4$ solution with weight of 2.2 kg containing 15 weight % of palladium and an aqueous $CuCl_2$ solution with weight of 0.5 kg containing 14.6 weight % of copper were prepared.

This catalyst was evaluated by the same method as in Example 4, and the results are listed in Table 1.

COMPARATIVE EXAMPLE 3

The catalyst was prepared by the same method as in Example 1 except that, in step 1), an aqueous $Na_2PdCl_4$ solution with weight of 2.2 kg containing 15 weight % of palladium and an aqueous $HAuCl_4$ solution with weight of 0.5 kg containing 30 weight % of gold were prepared.

This catalyst was evaluated by the same method as in Example 1, and the results are listed in Table 1.

COMPARATIVE EXAMPLE 4

The catalyst was prepared by the same method as in Example 1 except that, in step 1), an aqueous $Na_2PdCl_4$ solution with weight of 2.2 kg containing 15 weight % of palladium and an aqueous $CuCl_2$ solution with weight of 0.5 kg containing 14.6 weight % of copper were prepared.

This catalyst was evaluated by the same method as in Example 1, and the results are listed in Table 1.

COMPARATIVE EXAMPLE 5

The catalyst was prepared by the same method as in Example 1 except that, in step 1), an aqueous $Na_2PdCl_4$ solution with weight of 2.2 kg containing 15 weight % of palladium, an aqueous $HAuCl_4$ solution with weight of 0.5 kg containing 30 weight % of gold and an aqueous $CuCl_2$ solution with weight of 0.67 kg containing 15 weight % of copper were prepared.

This catalyst was evaluated by the same method as in Example 1, and the results are listed in Table 1.

TABLE 1

| Item | STY-1 (g/l/hr) | STY-2 (g/l/hr) | Relative Ratio | Selectivity (%) |
| --- | --- | --- | --- | --- |
| Example 1 | 400 | 355 | 0.887 | 94.8 |
| Example 2 | 323 | 204 | 0.632 | 91.6 |
| Example 3 | 350 | 225 | 0.643 | 92.5 |
| Example 4 | 410 | 368 | 0.898 | 95.1 |
| Comparative Example 1 | 400 | 312 | 0.780 | 91.9 |
| Comparative Example 2 | 420 | 353 | 0.840 | 94.5 |
| Comparative Example 3 | 375 | 122 | 0.325 | 92.8 |
| Comparative Example 4 | 450 | 162 | 0.360 | 95.1 |

TABLE 1-continued

| Item | STY-1 (g/l/hr) | STY-2 (g/l/hr) | Relative Ratio | Selectivity (%) |
|---|---|---|---|---|
| Comparative Example 5 | 385 | 200 | 0.519 | 94.7 |

Note:
1. STY-1: Space time yield of allyl acetate after the oxacylation reaction was carried out for 6 hours.
2. STY-2: Space time yield of allyl acetate after the oxacylation reaction was carried out for 120 hours.
3. Relative ratio: The catalytic activity deteriorating ratio of STY-2 to STY-1.

It is seen clearly from the above Examples and Comparative Examples that, the activity of the traditional catalyst (see Comparative Examples 1 to 5, wherein gold or copper was used as the catalysis promoter) deteriorates rapidly when water is not added during the oxacylation process. As to the catalyst for oxacylation produced in the present invention, whether only tin, or the mixture of tin/gold or tin/copper is used as the promoter, superior catalytic activity deteriorating ratios are obtained when water is not added during the oxacylation process.

Therefore, in the presence of the catalyst produced in this invention, while no water is added into the reactant materials for the oxacylation process, or if only a small amount of water is added in accordance with the requirement of the process, not only can the catalytic activity and life of the catalyst be retained and not deteriorate, but high catalytic activity and high selectivity will be attained. Therefore, the energy consumed and wasted resulting from the addition of water can be avoided, and the economical effect of the oxacylation process can be greatly increased.

What is claimed is:

1. A vapor phase process for producing allyl acetate through oxacylation of propylene, acetic acid and oxygen in the presence of a catalyst with the condition that water is prevented from being added into reactant material for the oxacylation process, wherein the catalyst consists essentially of a porous carrier, 0.1 to 5.0 weight % of palladium metal as a main catalyst, 0 to 1.0 weight % of gold metal, and 0.01 to 5.0 weight % of tin metal as a promoter, based on the weight of said porous carrier, in combination with an alkali metal compound, supported on die outer surface of said porous carrier having a surface area of from about 100 to 120 $m^2/g$, and the total content of gold metal and tin metal based on the weight of said porous carrier is in the range of 0.01 to 5.0 weight %.

2. The process according to claim 1, wherein the content of said main catalyst, palladium metal, based on the weight of said porous carrier, is in the range 0.3 to 1.5 weight %.

3. The process according to claim 1, wherein the content of said promoter, tin metal, based on the weight of said porous carrier, is in the range of 0.02 to 1.0 weight %.

4. The process according to claim 1, wherein the total content of said promoter, tin metal and gold metal, based on the weight of said porous carrier, is in the range of 0.02 to 1.0 % by weight.

5. The process according to claim 1, wherein the content of said alkali compound, based on the weight of said porous carrier, is in the range of 1 to 15 weight %.

6. The process according to claim 5, wherein the content of said alkali compound, based on the weight of said porous carrier, is in the range of 4 to 10 weight %.

7. The process according to claim 1, wherein said alkali metal compounds are hydroxides, acetates, nitrates or bicarbonates of potassium, sodium, cesium, magnesium, or barium.

8. The process according to claim 7, wherein said alkali or alkaline metal compounds are hydroxide, acetate, nitrate and bicarbonate of potassium.

9. The process according to claim 1, wherein said porous carrier is selected from the group consisting of alumina, silica gel, silica, active carbon, silicon carbide, diatomaceous earth, pumice and a mixture thereof.

* * * * *